US008911980B2

(12) United States Patent
Suzuki et al.

(10) Patent No.: US 8,911,980 B2
(45) Date of Patent: Dec. 16, 2014

(54) METHOD FOR PRODUCING LIPASE POWDER COMPOSITIONS

(75) Inventors: Junko Suzuki, Yokohama (JP); Yoshie Yamauchi, Yokosuka (JP); Yuko Toyama, Yokosuka (JP); Satoshi Negishi, Yokosuka (JP)

(73) Assignee: The Nisshin Oillio Group, Ltd., Chuo-Ku, Tokyo (JP)

( * ) Notice: Subject to any disclaimer, the term of this patent is extended or adjusted under 35 U.S.C. 154(b) by 175 days.

(21) Appl. No.: 13/260,142

(22) PCT Filed: Mar. 26, 2010

(86) PCT No.: PCT/JP2010/055373
§ 371 (c)(1),
(2), (4) Date: Sep. 23, 2011

(87) PCT Pub. No.: WO2010/110424
PCT Pub. Date: Sep. 30, 2010

(65) Prior Publication Data
US 2012/0021483 A1  Jan. 26, 2012

(30) Foreign Application Priority Data
Mar. 27, 2009 (JP) ................................. 2009-077997

(51) Int. Cl.
| C12N 11/12 | (2006.01) |
| C12N 9/98 | (2006.01) |
| C12N 11/02 | (2006.01) |
| C12N 11/10 | (2006.01) |
| C12N 11/14 | (2006.01) |
| C12N 9/20 | (2006.01) |

(52) U.S. Cl.
CPC ...... *C12N 9/98* (2013.01); *C12N 11/02* (2013.01); *C12N 11/12* (2013.01); *C12N 11/10* (2013.01); *C12N 11/14* (2013.01); *C12N 9/20* (2013.01); *C12Y 301/01003* (2013.01)
USPC ........... 435/179; 435/176; 435/177; 435/178; 435/198

(58) Field of Classification Search
CPC .......... C12N 9/98; C12N 11/02; C12N 11/10; C12N 11/12; C12N 11/14; C12N 9/20
USPC .......................... 435/176, 177, 187, 179, 198
See application file for complete search history.

(56) References Cited

U.S. PATENT DOCUMENTS

| 4,798,793 A | 1/1989 | Eigtved |
| 4,818,695 A | 4/1989 | Eigtved |
| 5,166,064 A | 11/1992 | Usui et al. |
| 5,480,787 A | 1/1996 | Negishi et al. |
| 6,399,059 B1 | 6/2002 | Minoshima et al. |
| 2002/0078623 A1* | 6/2002 | Raddon ........................... 44/590 |
| 2006/0138256 A1* | 6/2006 | Horigane et al. ............... 241/23 |
| 2007/0196502 A1* | 8/2007 | Mort et al. ..................... 424/490 |
| 2008/0102500 A1 | 5/2008 | Negishi et al. |
| 2009/0075349 A1 | 3/2009 | Negishi et al. |

FOREIGN PATENT DOCUMENTS

| CN | 101194014 | | 6/2008 |
| EP | 0 322 213 | A2 | 6/1989 |
| EP | 0 648 495 | A2 | 4/1995 |
| JP | 60-098984 | A | 6/1985 |
| JP | 61-202688 | A | 9/1986 |
| JP | 1-262795 | A | 10/1989 |
| JP | 2-138986 | A | 5/1990 |
| JP | 3-061485 | A | 3/1991 |
| JP | 7-090002 | A | 4/1995 |
| JP | 2668187 | B2 | 7/1997 |
| JP | 11-100223 | A | 4/1999 |
| JP | 2000-106873 | A | 4/2000 |
| JP | 2007-124933 | A | 5/2007 |
| JP | 2007300855 | A * | 11/2007 |
| JP | 2008-022744 | A | 2/2008 |
| JP | 2008022744 | A * | 2/2008 |
| TW | 200813229 | | 3/2008 |
| WO | WO 2006/132260 | A | 12/2006 |
| WO | WO 2007/132775 | A1 | 11/2007 |

OTHER PUBLICATIONS

Machine translation of JP 2008022744 A downloaded from the JPO website on Apr. 20, 2013.*
Translation of JP 2007-300855 downloaded from the JPO Aug. 3, 2014.*
International Search Report (PCT/ISA/210) issued on Apr. 27, 2010, by Japanese Patent Office as the International Searching Authority for International Application No. PCT/JP2010/055373.
Written Opinion (PCT/ISA/237) issued on Apr. 27, 2010,, by Japanese Patent Office as the International Searching Authority for International Application No. PCT/JP2010/055373.
Taiwanese Office Action issued on Nov. 18, 2013.

* cited by examiner

*Primary Examiner* — Susan Hanley
(74) *Attorney, Agent, or Firm* — Buchanan, Ingersoll & Rooney PC

(57) ABSTRACT

The present invention provides a method for producing a ground product of a lipase powder composition comprising an immobilized lipase in which a lipase derived from *Thermomyces* sp. is immobilized to a silica carrier and a hydrophilic powder other than a silica carrier, the method comprising the steps of wetting the hydrophilic powder with oil; separating the hydrophilic powder wetted with oil from the oil to obtain an oil-containing hydrophilic powder; mixing the oil-containing hydrophilic powder and the immobilized lipase at a ratio of 0.45:1 to 0.85:1 based on mass of the hydrophilic powder and the immobilized lipase before oil wetting; and grinding the obtained mixture, the steps being conducted in the above order.

4 Claims, No Drawings

METHOD FOR PRODUCING LIPASE POWDER COMPOSITIONS

TECHNICAL FIELD OF THE INVENTION

The present invention relates to methods for producing a lipase powder composition, according to which it becomes possible to grind an immobilized lipase with reduced generation of dust.

BACKGROUND OF THE INVENTION

Lipases are widely used in esterification of various carboxylic acids such as fatty acids with alcohols such as monoalcohols and polyalcohols, transesterification between esters of several carboxylic acids, and the like. Among them, the transesterification reaction is an important technology not only as method for modifying animal and vegetable fats and oils but also as method for producing esters of various fatty acids such as sugar esters and steroids. When a lipase, which is a fat and oil hydrolase, is used as a catalyst in the above reactions, the transesterification reaction can be conducted under the mild condition, i.e. at room temperature to about 70° C. Therefore, the reactions using a lipase can better inhibit side reactions and reduce energy costs as compared with the conventional chemical reactions. In addition to it, since a lipase as a catalyst is a natural product, it is highly safe. Further, intended compounds can be effectively produced by using a lipase due to the substrate specificity and positional specificity thereof.

In order to evenly disperse such lipase in an oily raw material and to conduct transesterification in high activity, the technology has been developed comprising the steps of immobilizing a lipase to a carrier, grinding the immobilized lipase, and using the same (Patent Literature 1). However, a lipase sometimes causes allergic symptoms due to contact thereof to the skin or the suction thereof by breathing. In the production of an immobilized lipase powder composition, a lot of dust is generated in the step of grinding an immobilized lipase and, as a result, allergic symptoms are concerns. Thus, there is need to ensure safety of workers.

Patent Literature 1 WO 2006/132260 A

DISCLOSURE OF THE INVENTION

The object of the present invention is to provide a method for producing a ground product of a lipase powder composition, according to which it becomes possible to grind an immobilized lipase with reduced generation of dust and without generating smoke or unusual odor of a raw material to be ground.

The present invention has been completed based on the finding that the above problem can be solved by specifying, in the production of a ground product of a lipase powder composition comprising an immobilized lipase and a hydrophilic powder such as cellulose, the ratio of the immobilized lipase and the hydrophilic powder and the procedures of oil wetting when conducting wet grinding.

Accordingly, the present invention provides a method for producing a ground product of a lipase powder composition comprising an immobilized lipase in which a lipase derived from *Thermomyces* sp. is immobilized to a silica carrier and a hydrophilic powder other than a silica carrier, the method comprising the steps of wetting the hydrophilic powder with oil; separating the hydrophilic powder wetted with oil from the oil to obtain an oil-containing hydrophilic powder; mixing the oil-containing hydrophilic powder and the immobilized lipase at a ratio of 0.45:1 to 0.85:1 based on mass of the hydrophilic powder and the immobilized lipase before oil wetting; and grinding the obtained mixture, the steps being conducted in the above order.

The present invention also provides a method for grinding an immobilized lipase in which a lipase derived from *Thermomyces* sp. is immobilized to a silica carrier, the method comprising the steps of mixing an oil-containing hydrophilic powder obtained by wetting a hydrophilic powder with oil to the immobilized lipase at a ratio of 0.45:1 to 0.85:1 based on mass of the hydrophilic powder and the immobilized lipase before oil wetting; and grinding the mixture thereof.

According to the present invention, it becomes possible to appropriately grind an immobilized lipase with reduced generation of dust and without generating smoke or unusual odor of a raw material to be ground.

BEST MODE FOR CARRYING OUT THE INVENTION

An immobilized lipase used in the present invention is the lipase wherein a lipase derived from *Thermomyces* sp. is immobilized to a silica carrier. The average particle diameter of the immobilized lipase is preferably around 300 to 1000 μm. Such immobilized lipase can be obtained as Lipozyme TL-IM produced by Novozymes Japan Ltd., for example.

On the other hand, a hydrophilic powder used in the present invention is preferably a powder functioning as a filter aid and also having the function of reducing generation of dust. For example, inorganic filter aids such as Celite or organic filter aids such as fibers e.g. cellulose and ground products thereof can be preferably used for the above purposes. Among them, organic filter aids, particularly organic polymeric filter aids are preferable, and cellulose is further more preferable.

Cellulose used in the present invention is not particularly limited, and it is possible to use cellulose marketed as a trade name: KC Flock by Nippon Paper Chemicals Co., Ltd, for example. It is preferable that cellulose is powdery and has the average particle diameter of 10 to 90 μm.

In the production method of the present invention, a hydrophilic powder such as cellulose is first wetted with oil. The type of oil is not particularly limited as long as it can wet a hydrophilic powder to the extent that wet grinding can be appropriately conducted to a lipase and a hydrophilic powder used in the present invention. Edible oils are preferably used, such as rapeseed oil, MCT (triglycerides of medium-chain saturated fatty acids), soybean oil, sunflower oil, safflower oil, corn oil, cotton seed oil, grape seed oil, rice bran oil and mixtures thereof. As the edible oils, unrefined oil, deacidified oil, bleached oil, dewaxed oil or deodorized oil can be used. Among them, a mixture of bleached rapeseed oil and MCT is preferable, and a ratio (by mass) of bleached rapeseed oil and MCT in the mixture is preferably around 5:1 to 10:1, for example, around 9:1.

As for the amount of oil to a hydrophilic powder, those skilled in the art can appropriately determine the amount in which a hydrophilic powder are evenly mixed with oil and wetted. For example, a hydrophilic powder can be sufficiently wetted with oil by adding oil 2.4 to 3.0 times the mass of a hydrophilic powder and more specifically around 2.5 times thereof.

Next, the hydrophilic powder wetted with oil as mentioned above is separated from oil to obtain an oil-containing hydrophilic powder. Filtration, centrifugation, or the like can be used as the separation method, among which filtration is preferable. The method of filtration is not particularly limited and can be determined by those skilled in the art. It is possible to efficiently remove oil by pressure filtration and obtain a cake oil-containing hydrophilic powder. The degree of removal of oil by filtration will vary depending on the type of a hydrophilic powder and oil used. However, by removing oil so that an oil-containing amount of an oil-containing hydrophilic powder becomes around 1 to 1.4 times the mass of the hydrophilic powder before oil wetting, appropriate treatment can be conducted in the following step of grinding.

Next, the immobilized lipase is mixed with thus obtained oil-containing hydrophilic powder at a ratio of 0.45:1 to 0.85:1, preferably 0.45:1 to 0.7:1, and most preferably 0.5:1, based on mass of the hydrophilic powder and the immobilized lipase before oil wetting. By preparing the mixture within the above ratio, it is possible to appropriately grind the mixture with reduced generation of dust and without generating smoke or unusual odor of a raw material to be ground.

Thus obtained mixture is ground with common grinders. The grinders include mortars, friction-shear grinders, cutter grinders, millstones (mycolloiders, masscolloiders), coffee mills, power mills, pin mills, impact grinders (hammer mills, ball mills), roll mills and airflow mills, homogenizers, and ultrasonic grinders. In the present invention, pin mills are preferably used among them. For example, it is preferable to grind the mixture with Fine Impact Mill 100UPZ by HOSOKAWAMICRON CORPORATION in rotation speed of 10,000 to 12,000 rpm. The average particle diameter of the ground immobilized lipase obtained by the above grinding is 1 μm or more and less than 300 μm, preferably 1 to 200 μm, more preferably 1 to 100 μm, and particularly preferably 20 to 100 μm.

Further, in the present invention, the grinding is preferably conducted in the presence of dry ice. Dry ice is preferably ground in a powdery state and provided in a grinder so that it can be efficiently ground together with a mixture of an immobilized lipase and an oil-containing hydrophilic powder in the grinder. However, the degree of grinding dry ice may vary depending on the kind of a used grinder or the like.

Dry ice can be added upon starting the grinding, but since a mixture of an immobilized lipase and an oil-containing hydrophilic powder is continuously ground, it is preferable that dry ice exist throughout the step of grinding. Therefore, dry ice is preferably provided with frequent pauses or continuously in the step of grinding. Dry ice and the mixture can be mixed in advance and then provided in the grinder, or dry ice and the mixture can be separately provided in the grinder and then mixed and ground in the grinder.

Further, those skilled in the art can appropriately determine the amount of dry ice. In the case of using cellulose as a hydrophilic powder, it is possible to add dry ice 0.5 to 2.0 times the mass of a mixture of cellulose to be ground (a hydrophilic powder) and an immobilized lipase, and more preferably around the equivalent amount thereof throughout the step of grinding.

In the present invention, the generation of dust can be further reduced by conducting the step of grinding in the presence of dry ice as mentioned above.

According to the present invention comprising the steps of first wetting only a hydrophilic powder with oil, filtering it, and then grinding a mixture of the hydrophilic powder and an immobilized lipase when wet grinding a mixture of an immobilized lipase and a hydrophilic powder, it becomes possible to appropriately grind the mixture with highly reduced generation of dust as compared with the method comprising the steps of wetting, with oil, a mixture of an immobilized lipase and a hydrophilic powder mixed in advance, filtering and grinding it.

Next, Examples will further illustrate the present invention.

EXAMPLES

Examples 1 to 2, Comparative Examples 1 to 3

Consideration of the Ratio of a Hydrophilic Powder and an Immobilized Lipase

As a hydrophilic powder, 2500 g of KC Flock w-300G (cellulose powder: by Nippon Paper Chemicals Co., Ltd) was weighed out in a stainless steel mug. A mixed oil of 5580 g of bleached rapeseed oil (rapeseed oil: by The Nisshin OilliO Group, Ltd.) and 620 g of ODO (medium-chain triglyceride: by The Nisshin OilliO Group, Ltd.) was added thereto, and fully stirred until the cellulose and the oil were evenly mixed. Then, the mixed oil was removed by pressure filtration to obtain 5250 g of cellulose cake (an oil-containing hydrophilic powder).

The obtained cellulose cake and TL-IM (immobilized lipase: by Novozymes Japan Ltd.) were mixed in a plastic bag in accordance with the blend ratio in Table 1. Then, the mixture was ground with Fine Impact Mill 100UPZ (pin mill: by HOSOKAWAMICRON CORPORATION) in rotation speed of 10,000 to 12,000 rpm. The grinding conditions and generation of dust were examined and compared with each other. The results are shown in Table 1.

TABLE 1

| Ratio of cellulose powder and an immobilized lipase | | | | |
|---|---|---|---|---|
| | blend ratio | Status in grinding | | Overall |
| cellulose:TL-IM | (cake(g):TL-IM(g)) | grinding | dust | evaluation |
| 1:1 (Comparative Example 1) | 1050:500 | Generation of unusual odor and smoke in grinding; Clogging in a slot; Adherence of many chars to pin; Unusual odor in enzymes after grinding | No generation of dust | X |
| 0.8:1 (Example 1) | 840:500 | No unusual odor/smoke in grinding; Clogging in a slot; Adherence of some chars to pin | No generation of dust | ○ |

TABLE 1-continued

| | Ratio of cellulose powder and an immobilized lipase | | | |
|---|---|---|---|---|
| | blend ratio | Status in grinding | | Overall |
| cellulose:TL-IM | (cake(g):TL-IM(g)) | grinding | dust | evaluation |
| 0.5:1 (Example 2) | 525:500 | Generation of unusual odor and smoke in grinding; Little clogging in a slot; Adherence of little chars to pin | No generation of dust | ◎ |
| 0.4:1 (Comparative Example 2) | 420:500 | No unusual odor/smoke in grinding; No clogging in a slot; No adherence of chars to pin | Visually confirming dust | X |
| 0.3:1 (Comparative Example 3) | 315:500 | No unusual odor/smoke in grinding; No clogging in a slot; No adherence of chars to pin | Visually confirming dust | X |

\* Overall evaluation: X At least either the grinding or the dust is not in good condition.
○ Both of the grinding and the dust are in good conditions.
◎ Both of the grinding and the dust are in very good conditions.

As shown in Table 1, the conditions in Examples 1 and 2 are better than those in Comparative Examples 1 to 3 since the grinding is in good condition and the dust is not generated.

Comparative Examples 4 to 8

Consideration of the Order of Oil Wetting

The order of steps was changed so that a hydrophilic powder and an immobilized lipase were mixed and then wetted with oil, and the grinding was conducted.

TL-IM (immobilized lipase: by Novozymes Japan Ltd.) were weighed out in a stainless steel mug. Then, KC Flock w-300G (cellulose powder: by Nippon Paper Chemicals Co., Ltd) and a mixed oil of bleached rapeseed oil (rapeseed oil: by The Nisshin OilliO Group, Ltd.): ODO (medium-chain triglyceride: by The Nisshin OilliO Group, Ltd.)=9:1 were mixed thereto in the ratio of Table 2 and fully stirred. Then, the mixed oil was removed by pressure filtration to obtain a mixed cake of cellulose and enzymes. The cake was ground with Fine Impact Mill 100UPZ (pin mill: by HOSOKAWA-MICRON CORPORATION) in 10,000 to 12,000 rpm, and the grinding conditions were examined and compared with each other. The results are shown in Table 2.

TABLE 2

| Mixing cellulose powder and an immobilized lipase and then wetting them with oil (Comparative Examples 4 to 8) | | | | | | |
|---|---|---|---|---|---|---|
| cellulose: TL-IM | blend ratio (cake(g):TL-IM(g)) | Mixed oil (g) | wt. (g) of mixed cake after filtration | Status in grinding | | Overall evaluation |
| | | | | grinding | dust | |
| 1.5:1 (Comparative Example 4) | 300:200 | 1300 | 1120 | Exuding of oil at pin and becoming sticky; Strong deteriorated smell of oil | No generation of dust | X |
| 1:1 (Comparative Example 5) | 250:250 | 1300 | 1130 | Exuding of oil at pin and becoming sticky; Strong deteriorated smell of oil | No generation of dust | X |
| 0.8:1 (Comparative Example 6) | 400:500 | 2250 | 1662 | Grinding impossible due to clogging at pin soon after starting grinding | No generation of dust | X |
| 0.5:1 (Comparative Example 7) | 250:500 | 1900 | 1421 | Grinding impossible due to clogging in a slot | | X |
| 0.4:1 (Comparative Example 8) | 200:500 | 1750 | 1290 | Grinding impossible due to clogging in a slot | | X |

\* Overall evaluation: X At least either the grinding or the dust is not in good condition.
○ Both of the grinding and the dust are in good conditions.
◎ Both of the grinding and the dust are in very good conditions.

As shown in Table 2, the grinding is not in good condition in each of Comparative Examples 4 to 8.

Example 3

2000 g of KC Flock w-300G (cellulose powder: by Nippon Paper Chemicals Co., Ltd) was weighed out, and 4500 g of bleached rapeseed oil (rapeseed oil: by The Nisshin OilliO Group, Ltd.) and 500 g of ODO (medium-chain triglyceride: by The Nisshin OilliO Group, Ltd.) were added thereto and fully stirred. Then, pressure filtration was conducted to the mixture to obtain 4229 g of cellulose cake (an oil-containing hydrophilic powder). 4000 g of TL-IM (immobilized lipase: by Novozymes Japan Ltd.) was mixed with the cellulose cake, and ground with Fine Impact Mill 100UPZ (pin mill: by HOSOKAWAMICRON CORPORATION) in 10,000 to 12,000 rpm. The amount of the dust of 4 μm or less was measured by the gravimetric procedure in accordance with Working Environment Evaluation Standards of Industrial Safety and Health Act. The results are shown in Table 3.

Example 4

2000 g of KC Flock w-300G (cellulose powder: by Nippon Paper Chemicals Co., Ltd) was weighed out, and 4500 g of bleached rapeseed oil (rapeseed oil: by The Nisshin OilliO Group, Ltd.) and 500 g of ODO (medium-chain triglyceride: by The Nisshin OilliO Group, Ltd.) were added thereto and fully stirred. Then, pressure filtration was conducted to the mixture to obtain 4339 g of cellulose cake (an oil-containing hydrophilic powder). 4000 g of TL-IM (immobilized lipase: by Novozymes Japan Ltd.) was mixed with the cellulose cake, and ground with Fine Impact Mill 100UPZ (pin mill: by HOSOKAWAMICRON CORPORATION) in 10,000 to 12,000 rpm. Dry ice ground in a powdery state was intermittently poured to the mixture of the cellulose cake and TL-IM continuously ground with Fine Impact Mill 100UPZ at about 5-minute intervals, and ground together with the cellulose cake. Meanwhile, the poured amount of the dry ice each time was 100 to 130 g. The amount of the dust of 4 μm or less was measured by the gravimetric procedure in accordance with Working Environment Evaluation Standards of Industrial Safety and Health Act. The results are shown in Table 3.

Example 5

2000 g of KC Flock w-300G (cellulose powder: by Nippon Paper Chemicals Co., Ltd) was weighed out, and 4500 g of bleached rapeseed oil (rapeseed oil: by The Nisshin OilliO Group, Ltd.) and 500 g of ODO (medium-chain triglyceride: by The Nisshin OilliO Group, Ltd.) were added thereto and fully stirred. Then, pressure filtration was conducted to the mixture to obtain 4183 g of cellulose cake (an oil-containing hydrophilic powder). 4000 g of TL-IM (immobilized lipase: by Novozymes Japan Ltd.) was mixed with the cellulose cake, and ground with Fine Impact Mill 100UPZ (pin mill: by HOSOKAWAMICRON CORPORATION) in 10,000 to 12,000 rpm. 8000 g in total of dry ice ground in a powdery state was continuously poured to the mixture of the cellulose cake and TL-IM continuously ground with Fine Impact Mill 100UPZ, and ground together with the cellulose cake. The amount of the dust of 4 μm or less was measured by the gravimetric procedure in accordance with Working Environment Evaluation Standards of Industrial Safety and Health Act. The results are shown in Table 3.

Comparative Example 9

5000 g of TL-IM (immobilized lipase: by Novozymes Japan Ltd.) was ground with Fine Impact Mill 100UPZ (pin mill: by HOSOKAWAMICRON CORPORATION) in 10,000 to 12,000 rpm. Then, the amount of the dust of 4 μm or less was measured by the gravimetric procedure in accordance with Working Environment Evaluation Standards of Industrial Safety and Health Act. The results are shown in Table 3.

TABLE 3

Comparison of the amounts of dust

| | Example 3 | Example 4 | Example 5 | Comparative Example 9 |
|---|---|---|---|---|
| Amount of dust (mg/m³) | 0.43 | 0.027 | 0.0063 | 2.71 |

* Less the amount of the dust is better.

As shown in Table 3, the generated amount of the dust in each of Examples 3 to 5 is less than that of Comparative Example 9, and therefore, the working environment of said Examples is better.

What is claimed is:

1. A method for producing a ground product of a lipase powder composition comprising an immobilized lipase in which a lipase derived from *Thermomyces* sp. is immobilized to a silica carrier and a cellulose powder wherein the cellulose powder has an average particle diameter of 10 to 90 μm, the method comprising the steps of wetting the cellulose powder with oil; removing part of the oil from the cellulose powder wetted with oil so that the amount of oil remaining in the oil-containing cellulose powder is 1 to 1.4 times the mass of the cellulose powder before oil wetting; mixing the oil-containing cellulose powder and the immobilized lipase at a ratio of 0.45:1 to 0.85:1 based on mass of the cellulose powder and the immobilized lipase before oil wetting; and grinding the obtained mixture, the steps being conducted in the above order.

2. The method according to claim 1, wherein the step of grinding is conducted in the presence of dry ice.

3. The method according to claim 1, wherein the average particle diameter of the immobilized lipase in the ground product of the lipase powder is 1 μm or more and less than 300 μm.

4. A method for grinding an immobilized lipase in which a lipase derived from *Thermomyces* sp. is immobilized to a silica carrier, the method comprising the steps of: mixing (i) an oil-containing cellulose powder obtained by wetting a cellulose powder wherein the cellulose powder has an average particle diameter of 10 to 90μm with oil and removing part of the oil from the cellulose powder wetted with oil so that the amount of oil remaining in the oil-containing cellulose powder is 1 to 1.4 times the mass of the cellulose powder before oil wetting and (ii) the immobilized lipase at a ratio of 0.45:1 to 0.85:1 based on mass of the cellulose powder and the immobilized lipase before oil wetting; and grinding the mixture thereof the steps being conducted in the above order.

* * * * *